US008246946B2

(12) United States Patent
Cobb et al.

(10) Patent No.: US 8,246,946 B2
(45) Date of Patent: Aug. 21, 2012

(54) TREATMENT OF BIPOLAR DISORDER UTILIZING ANTI-FUNGAL COMPOSITIONS

(75) Inventors: Mark L. Cobb, Dallas, TX (US); Alyson Cobb, Dallas, TX (US)

(73) Assignee: Cobb & Associates, Dallas, TX (US)

( * ) Notice: Subject to any disclaimer, the term of this patent is extended or adjusted under 35 U.S.C. 154(b) by 1203 days.

(21) Appl. No.: 11/535,752

(22) Filed: Sep. 27, 2006

(65) Prior Publication Data
US 2007/0071739 A1    Mar. 29, 2007

Related U.S. Application Data

(60) Provisional application No. 60/720,869, filed on Sep. 27, 2005.

(51) Int. Cl.
*A01N 63/00* (2006.01)
*A01N 65/00* (2009.01)

(52) U.S. Cl. .................. 424/93.3; 424/93.1; 424/93.46; 424/93.462

(58) Field of Classification Search .................. 424/93.1, 424/93.3, 93.46, 93.462
See application file for complete search history.

(56) References Cited

U.S. PATENT DOCUMENTS

| | | | |
|---|---|---|---|
| 5,599,795 A | 2/1997 | McCann et al. | |
| 6,203,797 B1 | 3/2001 | Perry | |
| 6,207,703 B1 | 3/2001 | Ponikau | |
| 6,254,910 B1 * | 7/2001 | Paluch ........................ 426/282 |
| 6,312,746 B2 | 11/2001 | Paluch | |
| 6,399,114 B2 | 6/2002 | Foreman | |
| 6,447,772 B1 | 9/2002 | Houston | |
| 6,461,607 B1 | 10/2002 | Farmer | |
| 6,471,999 B2 | 10/2002 | Couzy et al. | |
| 6,551,633 B2 | 4/2003 | Couzy et al. | |
| 6,746,671 B2 | 6/2004 | Steidler et al. | |
| 6,811,786 B1 | 11/2004 | Farmer et al. | |
| 6,861,053 B1 | 3/2005 | Lin et al. | |
| 7,192,581 B2 | 3/2007 | Park et al. | |
| 7,731,976 B2 | 6/2010 | Cobb et al. | |
| 7,749,509 B2 | 7/2010 | Cobb et al. | |
| 7,759,105 B2 | 7/2010 | Cobb et al. | |
| 2002/0013270 A1 | 1/2002 | Bolte | |
| 2002/0022019 A1 | 2/2002 | Laulund | |
| 2003/0003107 A1 | 1/2003 | Farmer | |
| 2003/0031659 A1 | 2/2003 | Farmer | |
| 2003/0175305 A1 | 9/2003 | Garner et al. | |
| 2004/0047896 A1 | 3/2004 | Malnoe et al. | |
| 2004/0167062 A1 | 8/2004 | Bolte | |
| 2004/0170617 A1 * | 9/2004 | Finegold ........................ 424/93.45 |
| 2004/0175372 A1 | 9/2004 | Park et al. | |
| 2005/0100535 A1 | 5/2005 | Farmer et al. | |
| 2005/0100559 A1 | 5/2005 | Myatt et al. | |
| 2005/0153018 A1 | 7/2005 | Ubbink et al. | |
| 2006/0177424 A1 | 8/2006 | Cobb et al. | |
| 2007/0071739 A1 | 3/2007 | Cobb et al. | |
| 2007/0098744 A1 | 5/2007 | Knorr et al. | |
| 2007/0128178 A1 | 6/2007 | Corthesy-Theulaz et al. | |
| 2007/0141039 A1 | 6/2007 | Collins et al. | |
| 2007/0280910 A1 | 12/2007 | Cobb et al. | |
| 2007/0280911 A1 | 12/2007 | Cobb et al. | |
| 2007/0280912 A1 | 12/2007 | Cobb et al. | |
| 2010/0303782 A1 | 12/2010 | Cobb et al. | |

FOREIGN PATENT DOCUMENTS

| | | |
|---|---|---|
| EP | 0 508 701 A2 | 10/1992 |
| WO | 9854982 A1 | 12/1998 |
| WO | WO0193904 A1 | 6/2001 |
| WO | WO 01/93904 * | 12/2001 |
| WO | 0205829 A2 | 1/2002 |
| WO | 2007038466 A2 | 4/2007 |
| WO | WO2009026306 A2 | 2/2009 |

OTHER PUBLICATIONS www.uniprot.org, "*Entercoccus faecium* (scientific name), accessed at www.uniprot.org/taxonomy/1352", "www.uniprot.org", Jul. 20, 2009, pp. 1-2.

Kim, Y. et al. , "The Effects of Probiotics on Symptoms of Irritable Bowel Syndrome", "Korean J. Gastroenterology", Jun. 2006, pp. 413-419, vol. 47, No. 6 (Original Korean Text).

Kim, Y. et al. , "The Effects of Probiotics on Symptoms of Irritable Bowel Syndrome", "Korean J. Gastroenterology", Jun. 2006, pp. 413-419, vol. 47, No. 6 (English Abstract Only).

Inovative Fulfillment Solutions, "Nutraceutical News, accessed at www.ifssoultions.com/news20070708.html", Jul./Aug. 2007 , pp. 1-5, Publisher: Innovative Fulfillment Solutions.

Symbionforlife.Com, "SymbionTM Webpages from symbionforlife. com website, accessed Jul. 20, 2009", "symbionforlife.com", Jul. 20, 2009, pp. 1-27.

Tomkins, T. ET , "A comprehensive review of post-market clinical studies performed in adults with an Asian probiotic formulation", "Beneficial Microbes", 2009, Publisher: Wageningen Academic Publishers.

Trenev, N. , "Probiotics: Nature's Internal Healers", "Probitoics", 1998, pp. 129 132-133, Publisher: Avery Trade.

Bezkorovainy, A. , "Probiotics: determinants of survival and growth in the gut ", "Am. J. Clin. Nutr. ", 2001, pp. 399S-405S, vol. 73, Publisher: American Society for Clinical Nutrition.

Vecchi, E. et al., "*Lactobacillus* Sporogenes or *Bacillus* Coagulans Misidentification or Mislabelling?", "Int. Journal of Probiotics and Prebiotics ", 2006, pp. 3-10, vol. 1, No. 1.

(Continued)

*Primary Examiner* — Jon P Weber
*Assistant Examiner* — Thane Underdahl
(74) *Attorney, Agent, or Firm* — Hultquist, PLLC; Steven J. Hultquist; Kelly K. Reynolds

(57) ABSTRACT

A method for treatment or prophylaxis of a bipolar disorder disease state, by administration of an anti-fungal composition that includes at least one of the bacilli (1) *Bacillus subtilis*, (2) *Bacillus coagulans*, and (3) *Enterococcus faecium*.

7 Claims, No Drawings

OTHER PUBLICATIONS

"How does *candida* harm my body?", "First found online at http://www.1stcandidacure.com/candidacureplan.html", Aug. 26, 2004, Anonymous 1 pg.

"Chronic Fatigue, Fybromyalgia and other Autoimmune disease", "First found online at http://www.candidasupport.org/faq'sandingredie.html", Aug. 20, 2003, Anonymous 1 pg.

"Eliminate the underlying cause", "First found online at http://www.candidfree.net/pages/1/index.html", Sep. 21, 2004, Mark Cobb, 30 pgs.

"*Candida* Support", "Accessed Online Jun. 13, 2008 at: http://www.candidasupport.org/3lac.html", Jun. 13, 2008, Anonymous 19 pgs.

Chou, Yen-Yi, et al., "Vancomycin-resistant enterococcal bacteremia: comparison of clinical features and outcome between *Enterococcus faecium*. . . ", "J. Microbiol. Immunol. Infect.", Apr. 2008, pp. 124-129, vol. 41.

Edelson, Stephen M., "The candida yeast-autism connection", "First found online at http://www.autism.org/candida.html", Aug. 20, 2003.

"Global Health Trax Inc. website advertisement for Threelac product", "http://www.ghtdirect.com/threelac_main.aspx", 2007, Publisher: Global Health Trax Inc. website, Anonymous 3 pgs.

Harrison, Robert, "*Candida* Research Article", "Found online at http://www.candidayeastinfection.com/researcharticle.html", Jul. 13, 2007, 9 pgs.

"*Lactobacillus sporogenes*—Introduction to LactoSpore", "Found online at http://www.lactospore.com", Anonymous, 25 pgs.

Lewis, Carol, "Irritable Bowel Syndrome: A poorly understood disorder", "FDA Consumer Magazine", Jul.-Aug. 2001, pp. 1-9, Publisher: U.S. Food and Drug Administration.

"Primal Defense—Product Information", "First found online at http://www.forhealthsolutions.net/primal-defense.html", Aug. 20, 2003, Anonymous, 2 pgs.

"ThreeLac *Candida* Defense—How does Nature's Biotics help?", "First found online at http://www.gethealthyagain.com/candida", Aug. 20, 2003, Anonymous, 2 pgs.

"ThreeLac Study—Nine Month Results", "Accessed Online Jun. 12, 2008 at http://www.autism-study.com/", Jun. 12, 2008, Jang M. and Green J.A., 8 pgs.

Hong, H., et al., "The Use of Bacterial Spore Formers As Probiotics", "FEMS Microbiology Reviews", Dec. 16, 2004, pp. 813-835, vol. 29, No. 4.

Sanders, M., et al., "Sporeformers As Human Probiotics: *Bacillus, Sporolactobacillus*, and *Brevibacillus*", "Comprehensive Reviews in Food Science and Food Safety", Jul. 2003, pp. 101-110, vol. 2, No. 3.

\* cited by examiner

TREATMENT OF BIPOLAR DISORDER UTILIZING ANTI-FUNGAL COMPOSITIONS

CROSS-REFERENCE TO RELATED APPLICATION

The benefit of priority of U.S. Provisional Patent Application 60/720,869 filed Sep. 27, 2005 in the names of Mark L. Cobb and Alyson J. Cobb is hereby claimed under the provisions of 35 USC §119. The entire disclosure of said provisional application is hereby incorporated herein, for all purposes.

BACKGROUND OF THE INVENTION

The present invention in a broad aspect relates to a method for treatment of bipolar disorder, and more specifically to a method for treating a patient suffering from such disease state, involving administration of an anti-fungal bacteria composition to such patient.

DESCRIPTION OF THE RELATED ART

A variety of disease states and adverse physiological conditions have an etiological relationship to fungal exposure and infection. For example, candidiasis is a common fungal infection of mucosal membranes and other tissues. The infection is caused by the yeast-like organism *Candida*. Numerous species of *Candida* exist, including *C. albicans*. The recent increase in candidiasis is most likely caused by the rising incidence of AIDS, more intensive regimens of cancer therapy, complications of abdominal or cardio-thoracic surgery, organ transplantations, burns and trauma. In addition, immunocompromised individuals and women of childbearing age, especially pregnant women or women with one or more childbirths, are known to be more susceptible to microbial pathogenesis. Alteration of the fungi microenvironment, including changes in pH, temperature, osmotic pressure, and hormonal concentrations, is currently considered to be accountable for the initiation of *C. albicans* infection symptoms.

Women can contract vaginal candidiasis by engaging in sexual activity with men who may not be aware they are carrying the infection because the symptoms are so mild in men that they are either overlooked or are completely unfelt.

It has recently come to light that candidiasis strikes immunocompetent individuals as well. For example, the widespread use of anti-microbial agents, such as broad spectrum antibiotics, has resulted in a number of serious clinical consequences. For example, antibiotics can kill beneficial, non-pathogenic microorganisms (i.e., flora) within the gastrointestinal tract, but are powerless against the yeasts in the GI tract. As a result, the gastrointestinal yeasts normally kept in check by the flora begin to grow at an excessive rate. In addition to antibiotics, the unrestrained usage of steroids, birth control pills, antacid and anti-ulcer medications, as well as diets high in sugar have been blamed for the rapid rise in candidiasis in the general population. It is theorized that approximately 85% of Americans are or have been infected by some strain of yeast or fungus. Fungal infections can be systemic, subcutaneous, cutaneous or superficial (involving the outermost skin or hair).

Common candidiasis symptoms include, but are not limited to, fatigue or lethargy, depression, headaches, muscle aches, pain and/or swelling in the joints, irritability, memory loss, anxiety, and insomnia.

Fungal infections are among the most difficult to effectively treat and regimens must be continued for months before results can be seen. Currently, there are several different types of drugs on the market that can provide effective anti-fungal therapy, as well as anti-fungal diets, such as the four step *Candida* diet. The *Candida* diet includes: the immediate elimination of antibiotics, birth control pills and other hormone-altering substances; a low-sugar, low-carbohydrate, high protein diet; the medical use of anti-fungal agents such as nystatin; and the strengthening of the immune system through supplementation. Though often effective, anti-fungal drugs and the *Candida* diet are cost prohibitive to many and more often than not, the symptoms return upon termination of the regimen.

Manic depression or bipolar disorder is a neurological brain disorder involving extreme swings in mood, i.e., recycling between periods of mania and periods of depression. Manic depression is one of four mood disorders, the others being unipolar depressive disorder (depression only), unipolar disorder (mania only), and schizoaffective disorder (See Manual IV, American Psychiatric Association).

Currently, treating bipolar and unipolar disorders consists of a combination of psychotherapy, teaching learning life-adjustment skills, and using mood stabilizers such as lithium, and anticonvulsant medications such as valproic acid. The goal of the treatment is to effect a mental change in the person suffering from the disorder, from a state characterized by mood swings between mania and depression, to a stabilized state.

Lithium has a number of disadvantages including, but not limited to, the importance of establishing and maintaining the concentration of lithium in the blood, as well as a plethora or physiological conditions including hypothyroidism, tremors, dry mouth, weight gain, increased frequency of urination, nausea, impotence, decreased libido, diarrhea, kidney abnormalities, loss of appetite, visual impairment, seizures and arrhythmias. Valproic acid has been associated with hepatic dysfunction.

A highly derivable intervention would involve administration of a therapeutic agent that is safe and effective, without the attendant disadvantages of lithium and valproic acid to treat a patient with bipolar disorder for prevention or reduction of the biphasic mania/depression cycle and the stabilization of the patient in a mental state that is not subject to mood swings.

SUMMARY OF THE INVENTION

The invention generally relates to the therapeutic treatment of bipolar disorder and associated disease states and physiological conditions, as well as therapeutic compositions and kits comprising same.

In one aspect, the present invention relates to a method of treating a disease state including bipolar disorders comprising administering, to a subject in need thereof, an effective amount of a composition comprising at least one bacterial species for ameliorating or regulating the disease state.

In another aspect, the present invention relates to a method of treatment or prophylaxis of a bipolar disorder disease state comprising administering to a subject in need thereof, an effective amount of a composition comprising at least one of (1) *Bacillus subtilis*, (2) *Bacillus coagulans*, and (3) *Enterococcus faecium*. In one embodiment, when *Streptococcus faecalis* is present in the anti-fungal composition, *Bacillus subtilis* and/or *Bacillus coagulans* is also present.

In yet another aspect, the present invention relates to a therapeutic composition having utility for oral administration for treatment or prophylaxis of a bipolar disorder disease state comprising administering to a subject in need thereof, (i) an anti-fungal composition comprising at least one of (1) *Bacillus subtilis*, (2) *Bacillus coagulans*, and (3) *Enterococcus faecium*, and (ii) a non-microbial therapeutic agent effective for treatment or prophylaxis of bipolar disorder.

In a further aspect, the present invention relates to a kit for therapeutic intervention in treating or preventing a bipolar disorder disease state, said kit comprising:

(i) an anti-fungal composition comprising at least one of (1) *Bacillus subtilis*, (2) *Bacillus coagulans*, and (3) *Enterococcus faecium*; and (ii) instructions for the administration of the anti-fungal composition to a subject in need of treatment or prophylaxis of the bipolar disorder disease state.

Other aspects, features and embodiments of the invention will be more fully apparent from the ensuing disclosure and appended claims.

DETAILED DESCRIPTION OF THE INVENTION

The present invention relates to a method for treatment of disease states such as bipolar disorder, and more specifically to methods for treating a patient suffering from such disease state or other adverse physiological conditions comprising the administration of an effective dose of an anti-fungal bacteria composition to a patient in need of treatment thereof.

Applicants have unexpectedly discovered that the anti-fungal compositions of the present invention are able to effectively ameliorate and/or regulate bipolar disorders and many of the associated symptoms of said disorder.

The gastrointestinal microflora has been shown to play a number of vital roles in maintaining gastrointestinal tract function and overall physiological health. For example, the growth and metabolism of the many individual bacterial species inhabiting the gastrointestinal tract depend primarily upon the substrates available to them, most of which are derived from the diet. See e.g., Gibson G. R. et al., 1995. Gastroenterology 106: 975-982; Christi, S. U. et al., 1992. Gut 33: 1234-1238. These findings have led to attempts to modify the structure and metabolic activities of the community through diet, primarily with probiotics, which are live microbial food supplements. Probiotic microorganisms are those which confer a benefit when grown in a particular environment, often by inhibiting the growth of other biological organisms in the same environment. The best known probiotics are the lactic acid-producing bacteria (i.e., *Lactobacilli*) and *Bifidobacteria*, which are widely utilized in yogurts and other dairy products. These probiotic organisms are non-pathogenic and non-toxigenic, retain viability during storage, and survive passage through the stomach and small intestine. Since probiotics do not permanently colonize the host, they need to be ingested regularly for any health promoting properties to persist. Commercial probiotic preparations are generally comprised of mixtures of *Lactobacilli* and *Bifidobacteria*, although yeast such as *Saccharomyces* has also been utilized.

Although a potential link between bipolar disorder and gastrointestinal microflora has previously been a subject of speculation, no correlation has been scientifically proven. That said, the amelioration of gastrointestinal microflora may assist in the maintenance of a stable mental state.

The anti-fungal bacteria composition of the present invention includes lactic-acid producing bacteria and soil bacteria. In such composition, at least one of the bacilli *Bacillus subtilis, Enterococcus faecium*, and *Bacillus coagulans*, or a combination of two or more thereof, are contemplated herein.

Specifically, in the broad practice of the invention, the anti-fungal bacteria composition of the present invention may comprise, consist of, or consist essentially of one or more of *Bacillus subtilis, Enterococcus faecium*, and *Bacillus coagulans*. Preferably, all of such bacterial species are present in the formulation. An illustrative embodiment of the anti-fungal composition includes the anti-fungal bacteria composition sold under the trademark THREELAC, commercially available from Global Health Trax (Vista, Calif., USA).

The *Bacillus* species, particularly those species having the ability to form spores (e.g., *Bacillus coagulans*), are a preferred embodiment of the present invention. The ability to sporulate makes these bacterial species relatively resistant to heat and other conditions, provides for a long shelf-life in product formulations, and is ideal for survival and colonization of tissues under conditions of pH, salinity, and the like within the gastrointestinal tract. Additional useful properties of many *Bacillus* species include being non-pathogenic, aerobic, facultative and heterotrophic, thus rendering these bacterial species safe and able to readily colonize the gastrointestinal tract.

It should be noted that *Lactobacillus sporogenes* has recently been re-characterized as *Bacillus coagulans*. The initial classification as *Lactobacillus sporogenes* (see, Nakamura et al., *Int. J. Syst. Bacteriol.*, 38: 63-73, 1988) has been argued as incorrect due to the fact that the *Lactobacillus sporogenes* strain produces spores and through metabolic processes excretes L(+)-lactic acid, which under current classification rules requires that the bacterium be classified as a *bacillus* species. Furthermore, classic *Lactobacillus* species are normally unsuitable for colonization of the gut due to their instability in the harsh (i.e., acidic) pH environment of the bile, particularly human bile, but *Lactobacillus sporogenes* (*Bacillus coagulans*) is able to survive and colonize the gastrointestinal tract.

*Bacillus coagulans* is a non-pathogenic, Gram positive, spore-forming bacteria that produces L(+) lactic acid (dextrorotatory) under homo-fermentation conditions. It has been isolated from natural sources, such as heat-treated soil samples inoculated into nutrient medium (see e.g., Bergey's Manual of Systemic Bacteriology, Vol. 2, Sneath, P. H. A. et al., eds., Williams & Wilkins, Baltimore, Md., 1986). *Bacillus coagulans* has also been utilized to produce lactic acid (U.S. Pat. No. 5,079,164). Though not naturally found in the gut, *Bacillus coagulans* strains have been used as general nutritional supplements and agents to control constipation and diarrhea in humans and other animals.

*Bacillus coagulans* strains and their growth requirements have been described previously (see e.g., Baker, D. et al, *Can. J. Microbiol.*, 6: 557-563, 1960; Nakamura, H. et al, *Int. J Syst. Bacteriol.* 38: 63-73, 1988). In addition, various strains of *Bacillus coagulans* can be isolated from natural sources (e.g., heat-treated soil samples) using well-known procedures (see e.g., Bergey's Manual of Systemic Bacteriology, Vol. 2, p. 1117, Sneath, P. H. A. et al., eds., Williams & Wilkins, Baltimore, Md., 1986).

*Bacillus subtilis* is a Gram-positive, endospore-forming soil bacterium comprising aerobic and a few facultatively anaerobic rod-shaped bacteria. *Bacillus subtilis* was historically used to treat dysentery. It has been reported that ingested *Bacillus subtilis* are able to activate the human immune defense, including the IgM, IgG and IgA antibodies. *Bacillus subtilis* strains and their growth requirements are well known in the art.

*Enterococcus faecium* is a facultative anaerobic, Gram positive, cocci that produces L(+) lactic acid. The *Enterococcus faecium* strain is a natural inhabitant of the mammalian G.I. tract and causes many of the same problems as other members of the intestinal flora, including opportunistic urinary tract infections and wound infections.

The compositions of the invention comprising the bacilli (A) *Bacillus subtilis*, (B) *Enterococcus faecium*, and (C) *Bacillus coagulans*, or any combination thereof, are suitably administered to a subject in need of treatment in an amount sufficient to elicit an anti-fungal response or alternatively, to enhance an ongoing anti-fungal response. The compositions of the invention can also be administered to a subject in need of treatment in an amount sufficient to effectively ameliorate and/or regulate symptoms associated with other non-fungally related disease states or physiological conditions.

The invention contemplates compositions comprising the bacilli *Bacillus subtilis* ("A"), *Enterococcus feecium* ("B"), and *Bacillus coagulans* ("C"), in which each of such bacilli A, B and C may vary in relative amount with respect to one another, in various embodiments of the invention. For example, each of A, B and C may be present in an equal or equivalent amount, in relation to one anther. In other embodiments, A, B and C may be present in unequal amounts in relation to one another, with each of A, B and C being present in an amount in a range of from about 5% to about 90% by weight, based on the total weight of A, B and C, and with all amounts of A, B and C totaling 100%. Thus, the invention contemplates a wide variety of specific formulation embodiments, including by way of example the following illustrative compositions (showing percentages by weight for each of the A, B and C ingredients, based on the total weight of A+B+C in the composition):

| Weight percentages for each of A, B, C in Composition No: | A wt % | B wt % | C wt % | Total wt % of A, B and C |
|---|---|---|---|---|
| 1 | 30 | 30 | 40 | 100 |
| 2 | 25 | 40 | 35 | 100 |
| 3 | 25 | 50 | 25 | 100 |
| 4 | 25 | 70 | 5 | 100 |
| 5 | 20 | 40 | 40 | 100 |
| 6 | 20 | 50 | 30 | 100 |
| 7 | 20 | 60 | 20 | 100 |
| 8 | 10 | 50 | 40 | 100 |
| 9 | 10 | 60 | 30 | 100 |
| 10 | 10 | 80 | 10 | 100 |
| 11 | 5 | 80 | 15 | 100 |
| 12 | 5 | 90 | 5 | 100 |

Preferably, when *Enterococcus faecium* is present in the anti-fungal composition, *Bacillus subtilis* and/or *Bacillus coagulans* are also present.

The specific relative amounts of the active ingredients in the compositions of the invention will depend on a variety of factors known to those of skill in the art of therapeutic formulation. For example, factors to be considered include the route of administration and the nature of the subject to be treated. The effect of such factors, and other factors known in the art such as synergistic effects, is readily determined by one of skill in the art according to standard clinical techniques. Effective doses of the active components of the compositions of the present invention may also be extrapolated from dose-response curves derived from animal model test systems. Therapeutic results accumulated to date suggest that the gender and age of the subject are irrelevant to the overall efficacy of the composition, with the exception of patients less than six years of age, who are generally more responsive to the composition than any other age group.

The composition of the invention may be administered in any suitable dose amount that is effective to prevent, ameliorate, regulate, cure or otherwise treat the disease state or physiological condition in a subject in need of such therapeutic intervention.

In various specific embodiments, an effective dose of the anti-fungal composition of the present invention is about 1.0 g to about 15.0 g for an adult patient, more preferably between about 2.0 g and about 10.0 g. Effective doses are to be administered to a patient in need at least once a week, preferably once a day. Pediatric dosages may be in the range of 15% to 90% of adult dosages.

For example, some patients may administer a constant dosage of the anti-fungal composition over time, for example about 2 g to about 4 g per day, while some patients may choose to increase the dosage up to about 6 g to about 10 g per day, depending on the severity of the disease state or physiological condition. Once the disease state or physiological condition has been effectively ameliorated or regulated, the patient may decrease the dosage to about 2 g to about 4 g per day for maintenance purposes.

In general, the effective dosage of compositions of the invention for therapeutic use may be widely varied in the broad practice of the invention, depending on the specific application, condition, or disease state involved, as readily determinable within the skill of the art. By way of illustration, in some embodiments of the invention, the effective dosage of the composition may be in a range of from about 10 milligrams (mg) to 200 milligrams (mg) per kilogram body weight of the recipient per day. The desired dose may be presented in multiple (e.g., two, three, four, five, six, or more) sub-doses administered at appropriate intervals throughout the day. These sub-doses may be administered in unit dosage forms containing an appropriate amount of active ingredients per unit dosage form.

The anti-fungal compositions of the invention may additionally and optionally comprise any suitable adjuvants, excipients, additives, carriers, additional therapeutic agents, bioavailability enhancers, side-effect suppressing components, or other ingredients that do not preclude the efficacy of the composition for ameliorating or regulating the disease states or physiological conditions. Preferably, the bacilli (*Bacillus subtilis*, *Enterococcus faecium*, and *Bacillus coagulans*) comprise from about 50% to about 90% by weight of the composition, based on the total weight of the anti-fungal composition of the invention. Most preferably, the bacilli comprise from about 60% to about 80% by weight of the composition.

The compositions of the present invention suitable for oral administration may be presented as discrete units such as gelatin capsules or cachets, each containing a predetermined amount of the anti-fungal bacteria composition as a powder or granules.

Other routes of administration are contemplated including, but not limited to, subcutaneous, intramuscular, intradermal, transdermal, intraocular, intraperitoneal, mucosal, vaginal, rectal, and intravenous.

In addition, the compositions of this invention may further include one or more accessory ingredients selected from diluents, buffers, flavoring agents, binders, preservatives, and the like.

The invention further contemplates the provision of therapeutic compositions, including the aforementioned anti-fungal compositions in combination with other bipolar disorder treatment agents, e.g., lithium, anticonvulsant medications, antipsychotic medications, and combinations thereof, in additive as well as synergistic combinations.

In another aspect, the invention relates to a kit including the anti-fungal compositions of the invention, with or without other bipolar disorder treatment agents, and written indicia for dosage regimen.

The features and advantages of the invention are more fully shown by the following illustrative and non-limiting examples.

Example 1

A fifty-six year-old female patient with bipolar disorder reported experiencing suicidal tendencies and being unable to focus enough to read or solve problems. The patient's existing medication included large doses of anti-psychotic drugs. The patient orally administered approximately 2 g of the anti-fungal composition of the present invention per day with water. After three months, the patient's daily dosage of the anti-fungal composition was up to about 6 g per day and she was able to read and solve problems while simultaneously reducing the intake of anti-psychotic medications by half, and the patient reported that her suicidal tendencies had been reduced by the anti-fungal medication.

Example 2

A 56 year-old male patient with bipolar disorder was taking anti-anxiety and anti-depressants to maintain balance. The patient orally administered approximately 2 g of the anti-fungal composition of the present invention per day with water. After three months, the patient's daily dosage of the anti-fungal composition was up to about 6 g per day. The patient simultaneously eliminated sugar, bleached flour and gluten products from his diet, and was able to discontinue taking previously prescribed anti-anxiety and anti-depressant pharmaceuticals. Additionally, the patient reported the loss of feelings of hopelessness that had formerly plagued him.

While the invention has been described herein with reference to various specific embodiments, it will be appreciated that the invention is not thus limited, and extends to and encompasses various other modifications and embodiments, as will be appreciated by those ordinarily skilled in the art. Accordingly, the invention is intended to be broadly construed and interpreted, in accordance with the ensuing claims.

What is claimed is:

1. A method of treatment of a bipolar disorder disease state comprising orally administering to a human subject in need thereof, an effective amount of a bacterial composition whose bacterial species consist of (1) *Bacillus subtilis*, (2) *Bacillus coagulans*, and (3) *Enterococcus faecium*.

2. The method of claim 1, wherein an effective dose of said composition is administered at least once a day.

3. The method of claim 1, wherein an effective dose of said composition is from about 10 milligrams to about 200 milligrams per kilogram body weight of said human subject.

4. The method of claim 1, wherein an effective dose is encapsulated for administration.

5. The method of claim 1, wherein an effective dose is administered in a powder form.

6. The method of claim 1, wherein the bacterial composition comprises an additional ingredient selected from the group consisting of adjuvants, excipients, additives, carriers, additional therapeutic agents, bioavailability enhancers, and side-effect suppressing components.

7. A method of treatment of a bipolar disorder disease state comprising orally administering to a human subject in need thereof, an effective amount of a composition consisting of *Bacillus subtilis, Bacillus coagulans, Enterococcus faecium* and a carrier.

* * * * *